United States Patent
Anderson et al.

(10) Patent No.: US 12,060,315 B2
(45) Date of Patent: Aug. 13, 2024

(54) PRODUCTION PROCESSES OF S- AND O-DIACYLATED GAMMA-GLUTAMYL-CYSTEAMINE PRODRUGS

(71) Applicant: University of Sunderland, Sunderland (GB)

(72) Inventors: Rosaleen Joy Anderson, Sunderland (GB); Lisa Frost, Sunderland (GB); Neil Barnwell, Middlesbrough (GB); Matthew Levick, Middlesbrough (GB); Ivan Hales, Middlesbrough (GB); Michael Dunn, Middlesbrough (GB)

(73) Assignee: University of Sunderland, Sunderland (GB)

( * ) Notice: Subject to any disclaimer, the term of this patent is extended or adjusted under 35 U.S.C. 154(b) by 273 days.

(21) Appl. No.: 17/425,038

(22) PCT Filed: Feb. 14, 2020

(86) PCT No.: PCT/GB2020/050347
§ 371 (c)(1),
(2) Date: Jul. 22, 2021

(87) PCT Pub. No.: WO2020/165601
PCT Pub. Date: Aug. 20, 2020

(65) Prior Publication Data
US 2022/0106267 A1    Apr. 7, 2022

(30) Foreign Application Priority Data
Feb. 14, 2019 (GB) .................................... 1902018

(51) Int. Cl.
*C07C 327/30* (2006.01)

(52) U.S. Cl.
CPC .................. *C07C 327/30* (2013.01)

(58) Field of Classification Search
None
See application file for complete search history.

(56) References Cited

U.S. PATENT DOCUMENTS

| | | | |
|---|---|---|---|
| 5,624,955 | A | 4/1997 | Nagasawa et al. |
| 9,630,917 | B2 | 4/2017 | Nguyen |
| 10,485,774 | B2 | 11/2019 | Dohil et al. |
| 10,537,528 | B2 | 1/2020 | Dohil et al. |
| 10,905,662 | B2 | 2/2021 | Desjardin et al. |
| 2020/0268692 | A1 | 8/2020 | Stanton, Jr. et al. |

FOREIGN PATENT DOCUMENTS

| | | |
|---|---|---|
| EP | 3316877 B1 | 10/2019 |
| WO | 2015069888 A2 | 5/2015 |
| WO | 2016086103 A1 | 6/2016 |
| WO | 2018224813 A1 | 12/2018 |

OTHER PUBLICATIONS

Frost et al. "Synthesis of diacylated γ-glutamyl-cysteamine prodrugs, and in vitro evaluation of their cytotoxicity and intracellular delivery of cysteamine" European Journal of Medicinal Chemistry, 2016, vol. 109, pp. 206-215.*
Anthes et al. "An Improved Synthesis of a Selective Serotonin Reuptake Inhibitor" Organic Process Research & Development, 2008, vol. 12, No. 2, pp. 178-182.*
Berge et al., "Pharmaceutical Salts," Journal of Pharmaceutical Sciences, Jan. 1977, vol. 66, No. 1, pp. 1-19.
Higashiura et al., "Simple Peptides. Part 7. The Chemical Conversions of C-Terminal α-Amino Acids in Peptides into Unsubstituted or 2-Substituted Taurines via S-Acetylthio- or Halogeno-Intermediates," Journal of Chemical Research: Synopses, Jan. 1, 1992, No. 8, pp. 250-251.
Snider et al., "The (1-methyl)cyclopropyloxycarbonyl (MPoc) carbamate: a new protecting group for amines," Tetrahedron Letters, Apr. 6, 2011, vol. 52, No. 25, pp. 3171-3174.
International Search Report issued in corresponding International Patent Application No. PCT/GB2020/050347, mailed Apr. 16, 2020 (5 pages).
Anderson et al., "Design, Synthesis and Initial In Vitro Evaluation of Novel Prodrugs for the Treatment of Cystinosis," Letters in Drug Design & Discovery, 2006, vol. 3, No. 5, pp. 336-345.

* cited by examiner

*Primary Examiner* — Joseph R Kosack
(74) *Attorney, Agent, or Firm* — Greenberg Traurig, LLP; Chinh H. Pham; Natalie Salem

(57) ABSTRACT

Methods are provided for the synthesis of a compound of formula (X). $R^2$ is selected from —H, —$C_1$-$C_4$-alkyl, —$C_2$-$C_4$-alkenyl and $C_1$-$C_4$-aryl; $R^3$ is selected from —C(O)H and —C(O)$C_1$-$C_4$-alkyl; and A is a pharmaceutically acceptable anion (e.g. a halide). Also provided are intermediate compounds formed during the synthesis.

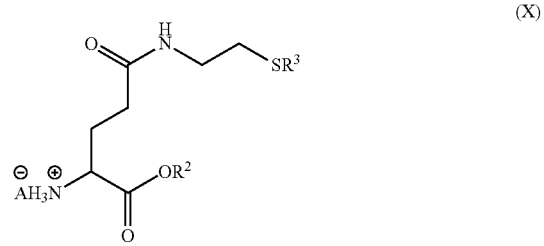

18 Claims, 2 Drawing Sheets

PRODUCTION PROCESSES OF S- AND O-DIACYLATED GAMMA-GLUTAMYL-CYSTEAMINE PRODRUGS

CROSS REFERENCE TO RELATED APPLICATIONS

This application is a U.S. National Phase patent application of PCT International Application No. PCT/GB2020/050347, filed Feb. 14, 2020, which claims priority to and the benefit of GB Application No. 1902018.9, filed on Feb. 14, 2019, the entire contents of each of which are hereby incorporated by reference in their entireties.

This invention relates to methods of synthesising prodrug derivatives of cysteamine.

BACKGROUND

Cysteamine is a treatment for the rare genetic disease cystinosis. The use of cysteamine as a treatment does, however, have several disadvantages which result in non-compliance in patients. Several prodrugs of cysteamine have been developed in an attempt to overcome these disadvantages. For example, the synthesis of diacylated γ-glutamyl-cysteamine prodrugs is demonstrated by L. Frost et al., *Eur. J. Med. Chem.*, 2016, 109, 206-215. Here, they investigate the therapeutic efficacy of a number of cysteamine prodrugs and their usefulness in treating cystinosis and provide methods of synthesising cysteamine prodrugs at small scale. These methods suffer from a number of disadvantages, such as modest yields. In addition, we have identified that there is a risk of contamination of the final product through hydrolysis of the thioester protecting groups producing pungent thiol by-products.

It is therefore desirable to find alternative and/or improved methods of synthesising cysteamine prodrugs.

BRIEF SUMMARY OF THE DISCLOSURE

The invention provides methods for the synthesis of derivatives of cysteamine, such as a compound of formula (X). The compound of formula (X) is typically provided as a salt, as this is expected to have a longer shelf life than the corresponding free base (compound of formula (IX)).

In accordance with a first aspect of the present invention there is provided a method of forming a compound of formula (X), the method comprising reducing a compound of formula (VI) to give a compound of formula (IX):

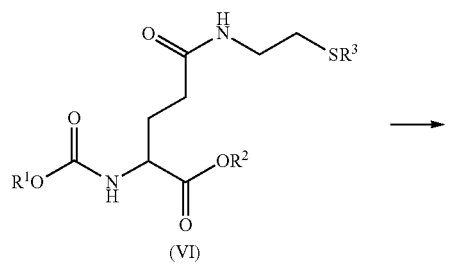

(VI)

and reacting the compound of formula (IX) with an acid of formula HA to provide the compound of formula (X):

(IX)

(IX)

(X)

$R^1$ is —$CH_2Ph$. $R^2$ is selected from —H, —$C_1$-$C_4$-alkyl, —$C_2$-$C_4$-alkenyl and —$C_1$-$C_4$-alkyl-aryl. The aryl may be a phenyl (Ph). $R^3$ is selected from —C(O)H and —C(O)$C_1$-$C_4$-alkyl. A is a pharmaceutically acceptable anion. This method separates formation of the free base (compound (IX)) and the salt form (X). An advantage of this is that, by choice of an appropriate acid HA, the skilled person can readily produce different salts of formula (X), which may allow fine tuning of properties, e.g. relating to one or more of compound stability, crystallinity, purity, chemical identity, hygroscopicity, odour in solution, solubility and dissolution profile.

In accordance with a second aspect of the present invention there is provided a method of forming a compound of formula (X), the method comprising: reacting a compound of formula (III) with the compound of formula (V) to form the compound of formula (VI):

(III) (V)

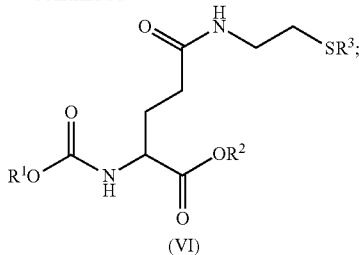

(VI)

and
cleaving the $R^1$-oxycarbonyl amide of the compound of formula (VI) with an acid (e.g. of formula HA) to form the compound of formula (X):

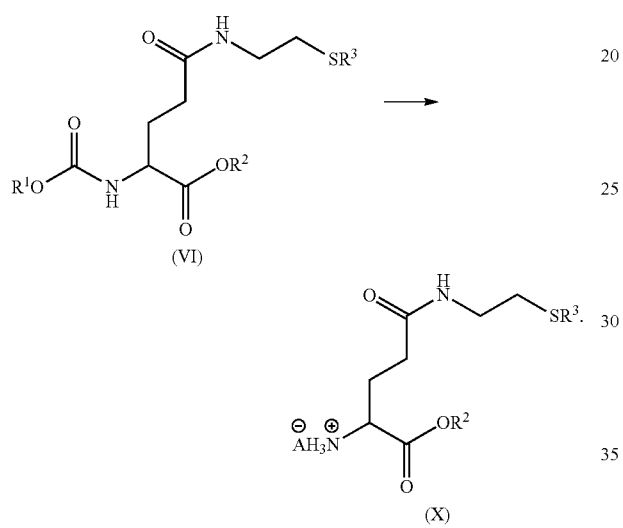

$R^1$ is —C(CH$_3$)$_3$. $R^2$ is selected from —H, —C$_1$-C$_4$-alkyl, —C$_2$-C$_4$-alkenyl, and —C$_1$-C$_4$-alkyl-aryl. The aryl may be a phenyl (Ph). $R^3$ is selected from —C(O)H and —C(O)C$_1$-C$_4$-alkyl. A is a halide or other counterion of a strong acid.

A third aspect of the present invention, provides a compound selected from

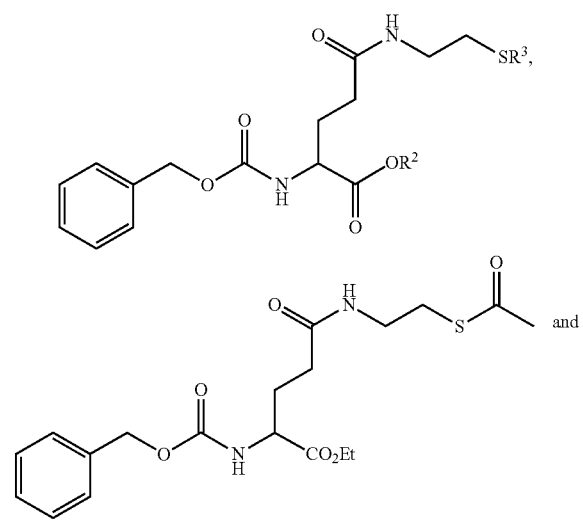

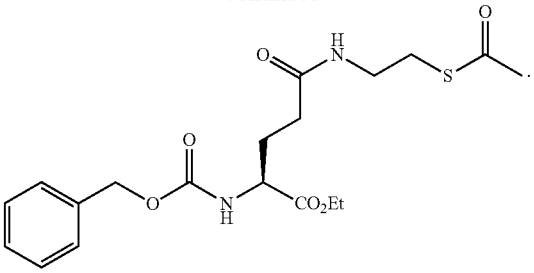

$R^2$ is selected from —H, —C$_1$-C$_4$-alkyl, —C$_2$-C$_4$-alkenyl and —C$_1$-C$_4$-alkyl-aryl. The aryl may be a phenyl (Ph). $R^3$ is selected from —C(O)H and —C(O)C$_1$-C$_4$-alkyl. These compounds are useful as intermediates in the synthesis of prodrug derivatives of cysteamine.

BRIEF DESCRIPTION OF THE DRAWINGS

Embodiments of the invention are further described hereinafter with reference to the accompanying drawings, in which.

DETAILED DESCRIPTION

Figure 1:
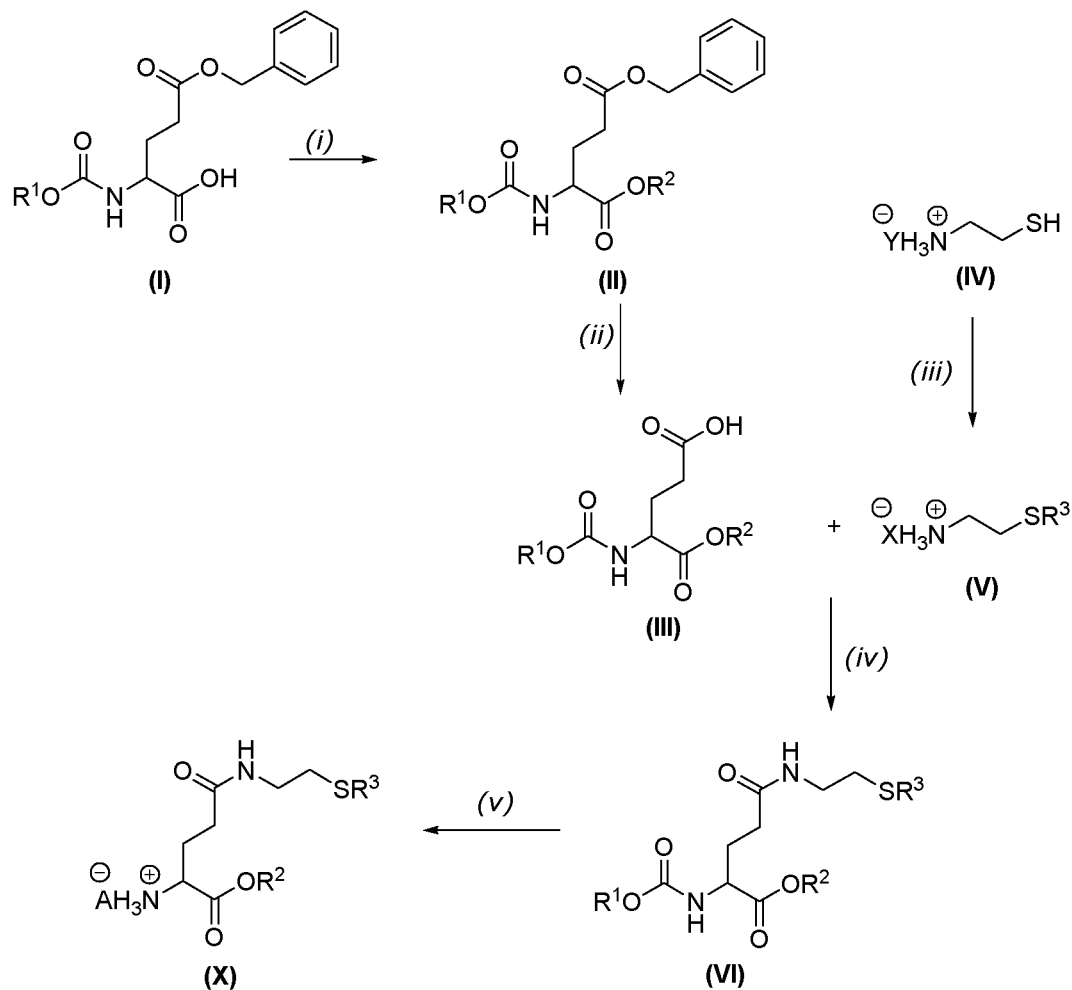
FIG. 1 provides Reaction Scheme 1 for the synthesis of a compound of formula (X).

The abbreviations used herein have their conventional meaning within the chemical and biological arts.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e.

unbranched) or branched chain, or combination thereof, which may be fully saturated, mono- or polyunsaturated and can include di- and multivalent moieties, having the number of carbon atoms designated (i.e. $C_1$-$C_{10}$ means one to ten carbons). Examples of saturated hydrocarbon moieties include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent moiety derived from an alkyl, as exemplified, but not limited, by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having 8 or fewer carbon atoms, for example having 6 or fewer (or 4 or fewer) carbon atoms.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Arylene" and "heteroarylene" refers to a divalent moiety derived from a aryl and heteroaryl, respectively.

The term "oxo" as used herein means an oxygen that is double bonded to a carbon atom.

The term "pharmaceutically acceptable salts" is meant to include salts of the active compounds which are prepared with relatively nontoxic acids or bases, depending on the particular substituents found on the compounds described herein. Exemplary pharmaceutically acceptable salts are provided in Pharmaceutical Salts: Properties, Selection and Use, 2011, Wiley, $2^{nd}$ Edition, ISBN 9783906390512. When compounds of the present invention contain relatively basic functionalities (such as one or more amine groups), acid addition salts can be obtained by contacting the neutral form of such compounds with a sufficient amount of the desired acid, either neat or in a suitable inert solvent. The desired acid may be a strong acid (e.g. hydrochloric acid, hydrobromic acid, sulfuric acid, phosphoric acid, mesylic acid, benzenesulfonic acid, 4-methylbenzenesulfonic acid, nosylic acid and the like) or a weak acid (e.g. acetic acid, maleic acid, fumaric acid, tartaric acid, citric acid, succinamic acid, lactic acid and the like). Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *J. Pharm. Sci.*, 1977, 66, 1-19). The anions provided by removing one or more hydrogen ions from these acids provide exemplary pharmaceutical acceptable anions. Compounds of formula (IX) described herein contain a primary amine and may be converted into an acid addition salt, e.g. of formula (X).

Thus, the compounds may exist as salts with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in the art, for example from the amine free base form of the compound (e.g. from a compound of formula (IX)).

The neutral forms of the compounds are preferably regenerated by contacting the salt with a base or acid and isolating the parent compound in the conventional manner. The parent form of the compound differs from the various salt forms in certain physical properties, such as solubility in polar solvents. This method does not, however, work well for compounds of formula (X), which represent acid addition salts of the compounds of formula (IX). The reason for this is that we have determined that compounds of formula (IX) have limited stability in base. Therefore reacting compounds of formula (X) with base results in the formation of various decomposition products of the compounds of formula (IX).

In addition to salt forms, the present invention provides methods of producing compounds, as well as compounds per se, which are in a prodrug form. A prodrug is a compound that readily undergoes chemical change under physiological conditions to provide an active compound of the present disclosure, such as cysteamine Additionally, prodrugs can be converted to active compounds of the present disclosure by chemical or biochemical methods in an ex vivo environment.

Certain compounds of the present disclosure or invention can exist in unsolvated forms as well as solvated forms, including hydrated forms. In general, the solvated forms are equivalent to unsolvated forms and are encompassed within the scope of the present invention. Certain compounds may exist in multiple crystalline or amorphous forms. In general, all physical forms are equivalent for the uses contemplated by the present disclosure.

Certain compounds disclosed herein possess asymmetric carbon atoms (optical centers) or double bonds; the racemates, diastereoisomers, tautomers, geometric isomers and individual isomers are encompassed within the scope of the present invention and the methods disclosed herein. The compounds of the present invention do not include those which are known in the art to be too unstable to synthesize and/or isolate.

The term "protecting group" as used herein is given its ordinary meaning which is readily understandable to those of skill in the art. It is used herein to refer to a group suitable for protecting a nitrogen or thiol. Exemplary protecting The reaction of step (iv) is typically performed in the presence of coupling agents, base and solvent. Surprisingly, we have identified that in step (iv), the relative amounts of the coupling agents, base and solvent used when performing the coupling reaction have a significant effect on the products formed. For example, using triethylamine (pK$_a$ 10.75) at 1 mol equiv. resulted in formation of an impurity, identified as an N/S-amide isomerisation product of compound (V). Using the weaker base N-methyl morpholine (pK$_a$ 7.38) at 0.8 mol equiv. resulted in a higher yield and significantly lower levels of N/S-amide isomerisation product impurity. Without wishing to be bound by any theory, it is believed that using a relatively strong base at stoichiometric or higher levels favours the following undesirable reaction (where R is H or alkyl, e.g. methyl):

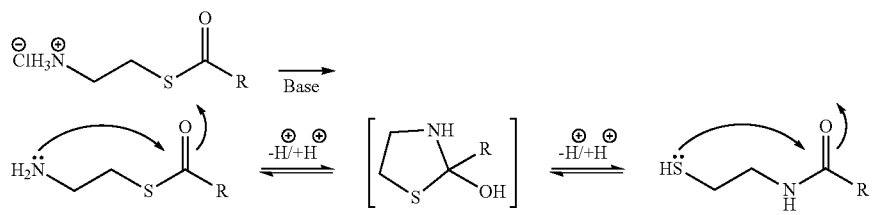

groups suitable for protecting a nitrogen include tert-butyloxycarbonyl group (BOC group) and benzylmethanoate group (PhCH$_2$OC(O)—). Exemplary protecting groups suitable for protecting a thiol include alkanal, e.g. —C(O)H or —C(O)C$_1$-C$_4$-alkyl.

It will typically be necessary to prepare the protected compounds by first protecting one moiety with a protecting group which is orthogonal to those which will be used to protect another moiety (i.e. a first protecting group can be removed without also removing a second protecting group).

The term "CF10" is used herein as a shorthand version of the compound 4-{[2-(S)-(acetylsulfanyl)ethyl]carbamoyl}-1-ethoxy-1-oxobutan-2-aminium chloride. If appropriate in a given context, CF10 may also refer to the base form of this compound, i.e. the compound 4-{[2-(S)-(acetylsulfanyl)ethyl]carbamoyl}-1-ethoxy-1-oxobutan-2-amine and/or pharmaceutically acceptable salts thereof.

The reader's attention is directed to all papers and documents which are filed concurrently with or previous to this specification in connection with this application and which are open to public inspection with this specification, and the contents of all such papers and documents are incorporated herein by reference.

The present invention provides methods for the synthesis of a compound of formula (X). A compound of formula (X) may be synthesised, for example, according to Reaction Scheme 1 or Reaction Scheme 2.

In Reaction Scheme 1 (FIG. 1), step (i) comprises reacting the compound of formula (I) with a base and an alkylating reagent of formula halo-R$^2$ to form a compound of formula (II). Step (ii) comprises reducing the compound of formula (II) to form a compound of formula (III). Step (iii) comprises adding a protecting group of formula —R$^3$ to the thiol group of the compound of formula (IV) to form a compound of formula (V). Step (iv) comprises reacting the compound of formula (III) with the compound of formula (V) to form the compound of formula (VI). Step (v) comprises cleaving the R$^1$-oxycarbonyl amide of the compound of formula (VI) to form the compound of formula (X). R$^1$ is —C(CH$_3$)$_3$ and A is a halide. R$^2$, R$^3$, X and Y are as defined herein.

It therefore may be advantageous in step (iv) to use a base having a pK$_a$ in water of less than about 9 (e.g. a pK$_a$ of about 7.2 to about 9). It therefore may be advantageous in step (iv) to use the base at a sub-stoichiometric amount. For example, the base may be provided in an amount of not more than 0.9 mol equiv. (such as 0.5 to 0.9 mol equiv., e.g. about 0.8 mol equiv.) compared to the compounds of formulae (III) and (V).

Figure 2:
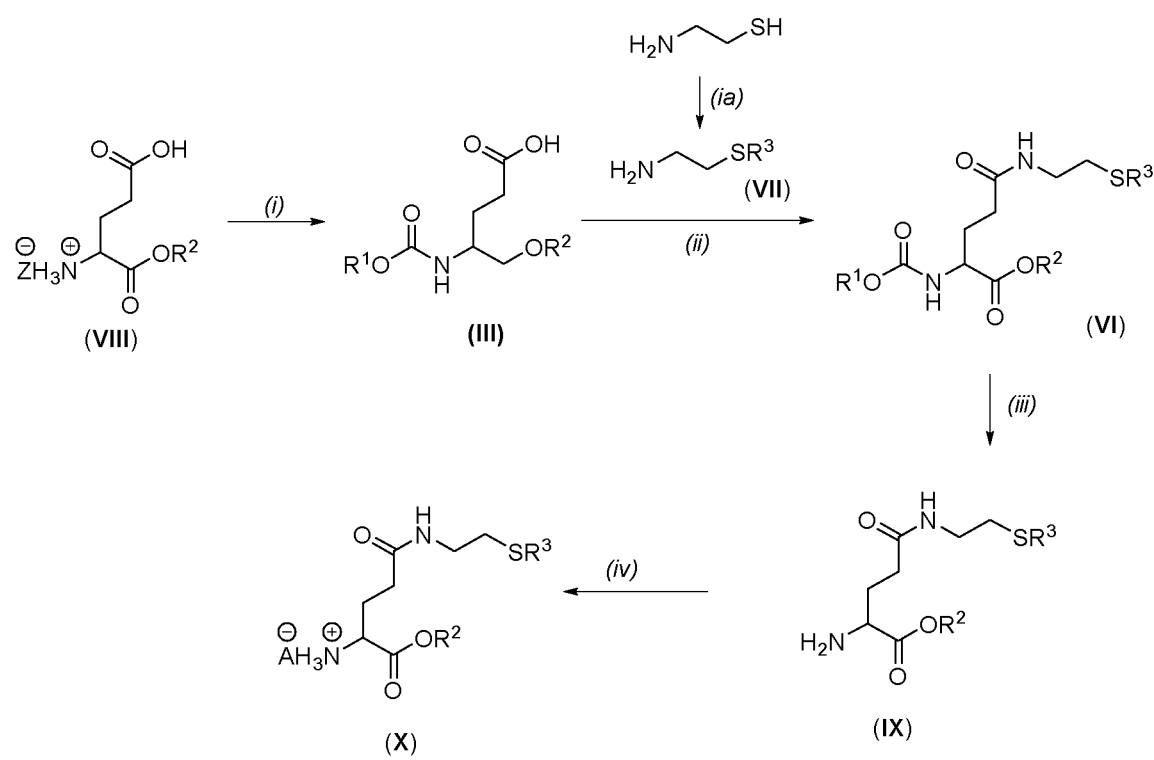
FIG. 2 provides Reaction Scheme 2 for the synthesis of a compound of formula (X).

In Reaction Scheme 2 (FIG. 2), step (i) comprises adding a protecting group of formula R$^1$—OC(O)— to the amine group of the compound of formula (VIII) to form the compound of formula (III). Step (ia) comprises adding a protecting group of formula —R$^3$ to the thiol group of the compound cysteamine to form a compound of formula (VII). Step (ii) comprises reacting the compound of formula (III) with the protected cysteamine formed in step (ia) to form the compound of formula (VI). Step (iii) comprises reducing the compound of formula (VI) to form a compound of formula (IX). Step (iv) comprises reacting a compound of formula (IX) with an acid, to form a compound of formula (X). R$^1$ is —CH$_2$Ph. R$^2$, R$^3$, A and Z are as defined herein.

As will be appreciated by the skilled person, Reaction Scheme 1 and Reaction Scheme 2 are stereospecific with the choice of appropriate starting materials. For example, the compound of formula (I) may be provided as the (S)-isomer in Reaction Scheme 1, wherein this stereochemistry would be retained in the compounds of formulae (II), (III), (VI) and (X). For example, the compound of formula (VII) may be provided as the (S)-isomer in Reaction Scheme 2, wherein this stereochemistry would be retained in the compounds of formulae (III), (VI), (IX) and (X).

In an embodiment the present invention provides a method of forming a compound of formula (X), the method comprising reducing a compound of formula (VI) to give a compound of formula (IX):

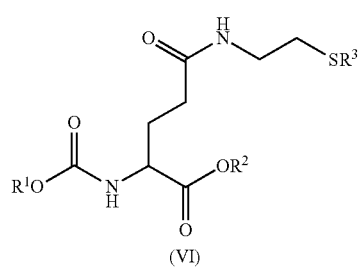

and
reacting the compound of formula (IX) with an acid of formula HA to provide the compound of formula (X):

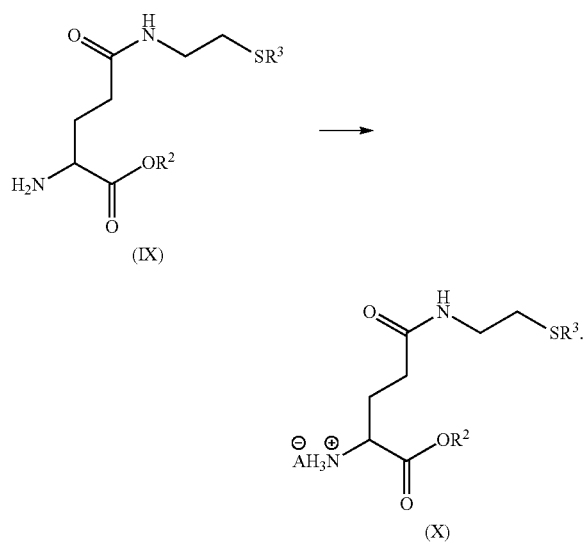

$R^1$ is —$CH_2Ph$. $R^2$ is selected from —H, —$C_1$-$C_4$-alkyl, —$C_2$-$C_4$-alkenyl and —$C_1$-$C_4$-alkyl-aryl. The aryl may be a phenyl (Ph). $R^3$ is selected from —C(O)H and —C(O)$C_1$-$C_4$-alkyl. A is a pharmaceutically acceptable anion.

$R^2$ may be selected from —H and —$C_1$-$C_4$-alkyl. $R^2$ may be —H. $R^2$ may be —$C_1$-$C_4$-alkyl. $R^2$ may be —$CH_3$. $R^2$ may be —$CH_2CH_3$. $R^2$ may be —$C_1$-$C_4$-alkyl-aryl, for example $R^2$ may be —$C_1$-$C_4$-alkyl-Ph. $R^2$ may be —$CH_2CH_2$-Ph, or —$CH_2$-Ph.

$R^3$ may be —C(O)$C_1$-$C_4$-alkyl. For example, $R^3$ may be —C(O)$CH_3$.

While A is indicated as a monovalent anion for convenience in formula (X), A may be a divalent or trivalent anion, in which case formula (X) is represented by formula (Xα) or formula (Xβ):

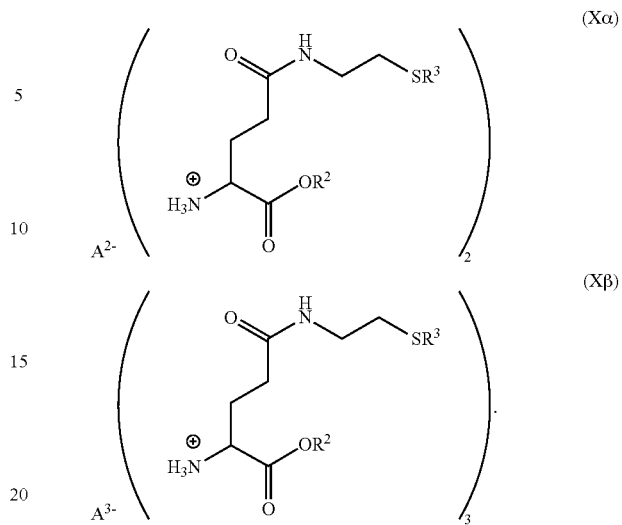

Unless indicated otherwise by the context, a reference to a compound of formula (X) includes reference to a compound of formula (Xα) and/or (Xβ).

A may be selected from halide (e.g. chloride, bromide), sulfate, methanesulfonate, nitrate, maleate, acetate, citrate, fumarate, tartrate, succinate, benzoate, glutamate and aspartate. A may be selected from chloride or bromide, e.g. chloride. A may be tartrate or fumarate.

Reducing the compound of formula (VI) may comprise dissolving the compound of formula (VI) in a suitable solvent and reducing the dissolved compound with $H_2$ in the presence of a catalyst. The solvent may be an alcohol or an ester, e.g. a $C_1$-$C_6$ alcohol or a $C_2$-$C_6$ ester. For example, the solvent may be selected from methanol, ethanol, propan-1-ol, propan-2-ol, butan-1-ol, butan-2-ol, methylethanoate and ethylethanoate. The catalyst may be an insoluble metal hydrogenation catalyst, e.g. Pd—C, $PtO_2$, or Ra—Ni. The $H_2$ may be provided at a pressure of 1 atm or greater. The reducing may be performed for a period of at least 1 hour.

Reacting the compound of formula (IX) with an acid of formula HA may comprise dissolving the compound of formula (IX) in a solution comprising the acid of formula HA. The solution may comprise a solvent that is or comprises an alcohol, e.g. a $C_1$-$C_6$ alcohol. For example, the solvent may be selected from methanol, ethanol, propan-1-ol, propan-2-ol, butan-1-ol, or butan-2-ol. The compound of formula (X) may be isolated from the solution using conventional means.

The compound of formula (VI) is formed by reacting a compound of formula (III) with a compound of formula (VII):

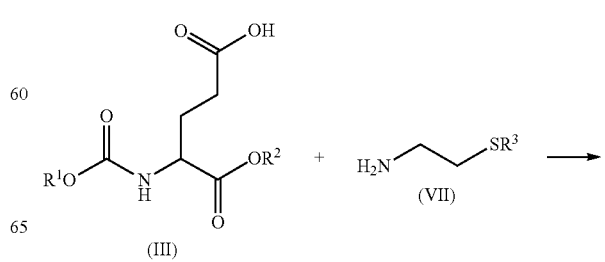

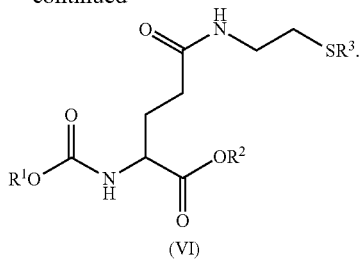

(VI)

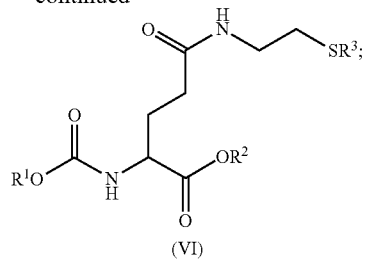

(VI)

The amide bond may be formed by dissolving the compounds of formulae (III) and (VII) in a suitable solvent system, activating the carboxyl group of the compound formula (III) and allowing the activated carboxyl to react with the amine group of the compound of formula (VII). Alternatively, the compound of formula (III) may be dissolved in a suitable solvent system, its carboxyl group may be activated and the compound of formula (VII) may then be added, thereby allowing the activated carboxyl to react with the amine group of the compound of formula (VII). A suitable activating agent is 1-ethyl-3-(3-dimethylaminopropyl)carbodiimide (EDCI). A suitable solvent system may comprise of or consist of at least one ester (e.g. ethylethanoate) or ether (e.g. tetrahydrofuran).

The compound of formula (VII) may be formed by alkylating or acylating the thiol of cysteamine. The alkylating may be performed by reacting a compound of formula $R^3$-halide or acylating by $R^3$—O—$R^3$ in the presence of a base with cysteamine.

The compound of formula (III) may be formed by adding a protecting group of formula $R^1$—OC(O)— to the amine group of a compound of formula (VIII):

(VIII)

wherein Z is a halide, optionally wherein Z is a chloride.

In an embodiment the present invention provides a method of forming a compound of formula (X), the method comprising reacting a compound of formula (III) with a compound of formula (V) to form the compound of formula (VI):

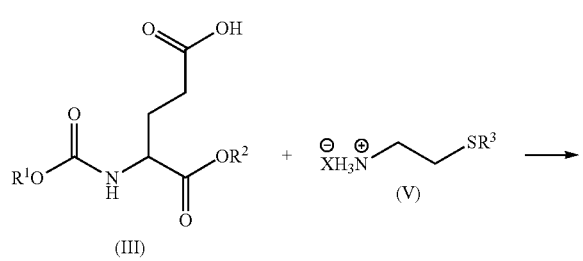

(III)          (V)

and
cleaving the $R^1$-oxycarbonyl amide of the compound of formula (VI) with an acid HA to form the compound of formula (X):

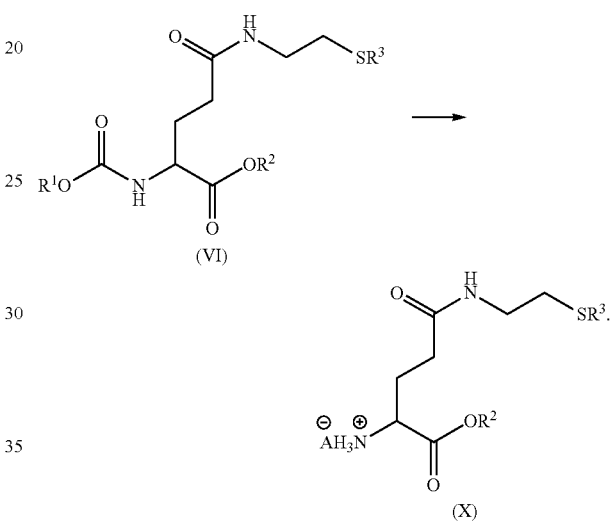

(VI)

(X)

$R^1$ is —C(CH$_3$)$_3$; $R^2$, $R^3$ and A are as defined herein. X is a halide.

The acid HA may be added to compound of formula (VI). The acid HA may be formed in situ. For example, an acid HA could be formed in situ from a solvent system comprising an acyl halide and an alcohol; e.g. acetyl chloride would react with isopropyl alcohol to generate HCl. Forming the acid in situ may provide advantages in material handling, providing a more readily scalable procedure.

Reacting the compound of formula (III) with the compound of formula (V) forms an amide bond. The amide bond may be formed by dissolving the compounds of formulae (III) and (V) in a suitable solvent system, activating the carboxyl group of the compound formula (III) and allowing the activated carboxyl to react with the amine group of the compound of formula (V). Alternatively, the compound of formula (III) may be dissolved in a suitable solvent system, its carboxyl group may be activated and the compound of formula (V) may then be added, thereby allowing the activated carboxyl to react with the amine group of the compound of formula (V). A suitable activating agent may be a carbodiimide, such as 1-ethyl-3-(3-dimethylaminopropyl)carbodiimide or dicyclohexylcarbodiimide. A suitable activating agent is 1-ethyl-3-(3-dimethylaminopropyl)carbodiimide. A suitable activating agent is dicyclohexylcarbodiimide. A suitable solvent system may comprise a halocarbon (e.g. dichloromethane). A suitable solvent system may comprise a base, e.g. an organic base. A mild base and/or a sub-stoichiometric amount of the base may be employed to minimise the undesirable isomerisation during the formation of the compound of formula (VI). A mild base may be an organic base having a p$K_a$ in water of less than about 9 (e.g. a p$K_a$ of about 7.2 to about 9). Exemplary mild organic bases include N-alkyl morpholines (e.g. N-methyl or N-ethyl morpholine), N-acyl piperazine, 1-alkylsulfonyl piperizine, 1-tosyl piperazine; e.g. N-methyl morpholine. A sub-stoichiometric amount of the base (less than 1 mol equiv.) may be a base provided in an amount of not more than 0.9 mol equiv. (such as 0.5 to 0.9 mol equiv., e.g. about 0.8 mol equiv.) compared to the compounds of formulae (III) and (V).

Cleaving the $R^1$-oxycarbonyl amide of the compound of formula (VI) with an acid may comprise dissolving the compound of formula (VI) in a solution comprising a solvent and an acid of formula HA and allowing the compound of formula (X) to form. The solvent may be an organic solvent. The solvent may comprise or consist of at least one $C_2$-$C_4$ ether (e.g. diethylether).

The compound of formula (V) may be formed by adding a protecting group of formula —$R^3$ to the thiol group of formula (IV).

Y is a halide. Adding a protecting group of formula —$R^3$ to the thiol group of the compound of formula (IV) may comprise reacting the compound with an anhydride of formula $R^3$—O—$R^3$. Adding a protecting group of formula —$R^3$ to the thiol group of the compound of formula (IV) may comprise reacting the compound with an acyl halide (e.g. acyl chloride) of formula $R^3$—Y.

The compound of formula (III) may be formed by reducing a compound of formula (II):

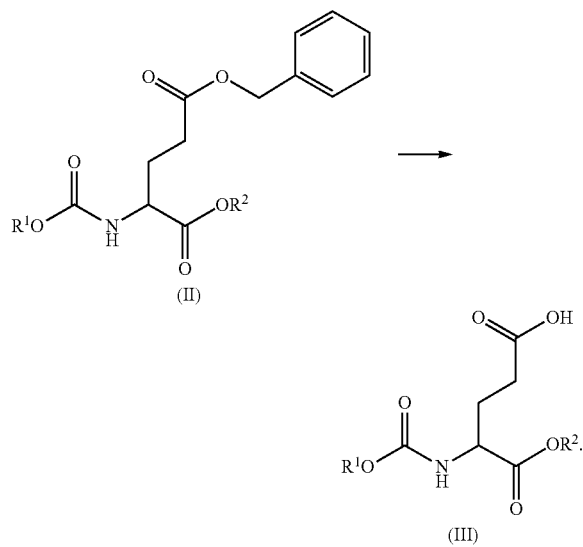

Reducing the compound of formula (II) may comprise dissolving the compound of formula (II) in a suitable solvent and reducing the dissolved compound with $H_2$ in the presence of a catalyst. The solvent may be an alcohol or an ester, e.g. a $C_1$-$C_6$ alcohol or a $C_2$-$C_6$ ester. For example, the solvent may be selected from methanol, ethanol, propan-1-ol, propan-2-ol, butan-1-ol, butan-2-ol, methylethanoate and ethylethanoate; e.g. the solvent may be methanol or ethanol. The solvent may be an alcohol of formula $R^2$—OH. Using an alcohol of formula $R^2$—OH may avoid impurities related to possible transesterification side reaction during reducing the compound of formula (II). The catalyst may be an insoluble metal hydrogenation catalyst, e.g. Pd—C, $PtO_2$, or Ra—Ni. The $H_2$ may be provided at a pressure of 1 atm or greater. The reducing may be performed for a period of at least 1 hour.

The compound of formula (II) may be formed by (i) reacting a compound of formula (I) with an alkylating reagent of formula halo-$R^2$:

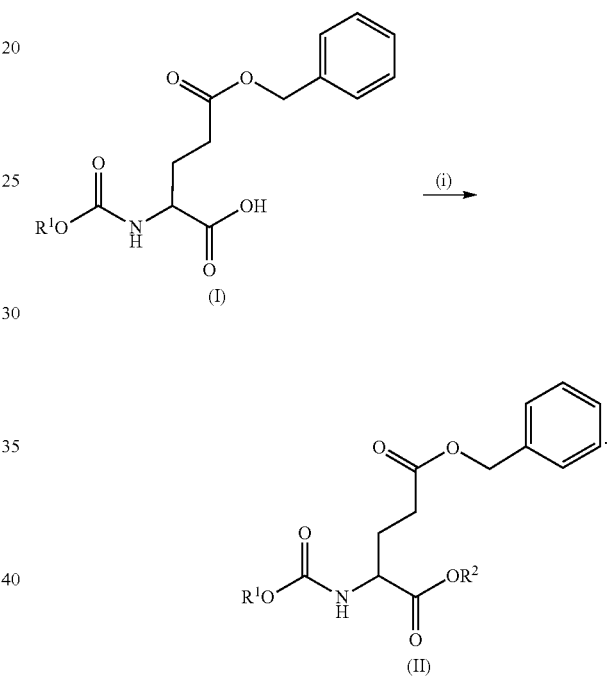

Converting a compound of formula (I) into a compound of formula (II) according to (i) may comprise dissolving the compound of formula (I) in a suitable solvent system and adding base until the pH is about 7 (e.g. a pH of 6.5-7.5). A suitable solvent system may comprise or consist of a halocarbon (e.g. dichloromethane). A suitable base may comprise aqueous carbonate (e.g. $Cs_2CO_3$). The mixture may then be treated with the alkylating reagent of formula halo-$R^2$.

$R^2$ may be selected from —H and —$C_1$-$C_4$-alkyl. $R^2$ may be —H. $R^2$ may be —$C_1$-$C_4$-alkyl. $R^2$ may be —$CH_3$. $R^2$ may be —$CH_2CH_3$. $R^2$ may be —$C_1$-$C_4$-alkyl-aryl, for example $R^2$ may be —$C_1$-$C_4$-alkyl-Ph. $R^2$ may be —$CH_2CH_2$-Ph, or —$CH_2$-Ph.

$R^3$ may be —C(O)$C_1$-$C_4$-alkyl. For example, $R^3$ may be —C(O)$CH_3$.

While A is indicated as a monovalent anion for convenience in formula (X), A may be a divalent or trivalent anion, in which case formula (X) is represented by formula (Xα) or formula (Xβ):

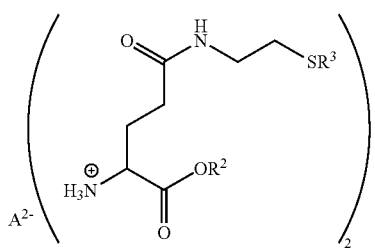

(Xα)

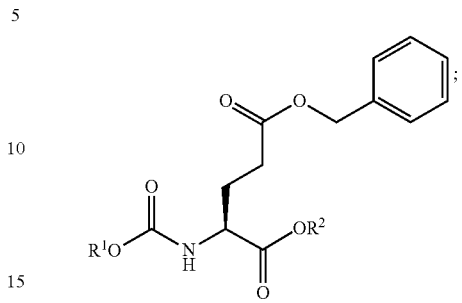

(IIa)

the compound of formula (II) may be a compound of formula (IIa):

and/or the compound of formula (III) may be a compound of formula (IIIa):

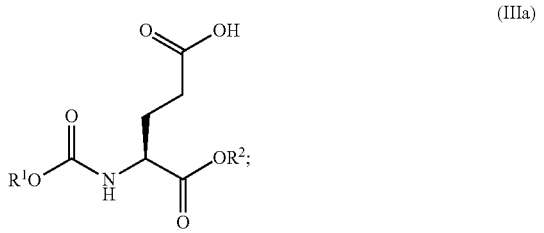

(IIIa)

(Xβ)

and/or the compound of formula (VI) may be a compound of formula (VIa):

Unless indicated otherwise by the context, a reference to a compound of formula (X) includes reference to a compound of formula (Xα) and/or (Xβ).

A may be selected from chloride, bromide, sulfate, phosphate, methanesulfonate, benzenesulfonate, tosylate, or nosylate. A may be a halide, for example A may be selected from chloride or bromide, e.g. chloride. A may be a counterion of a non-halide strong acid, for example A may be selected from sulfate, monohydrogensulfate, phosphate, monohydrogenphosphate, dihydrogenphosphate, methanesulfonate, benzenesulfonate, tosylate, or nosylate.

X may be chloride or bromide. X may be chloride.

Y may be chloride or bromide. Y may be chloride.

Z may be chloride or bromide. Z may be chloride.

The compounds of formulae (I), (II), (III), (VI), (VIII), (IX) and (X) each comprise an asymmetric (chiral) carbon. The disclosed methods accordingly include the racemates and optical isomers of these compounds. In particular, in accordance with the methods, the compound of formula (I) may be a compound of formula (Ia):

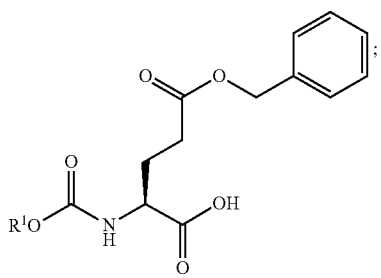

(Ia)

and/or (VIa)

and/or the compound of formula (IX) may be a compound of formula (IXa):

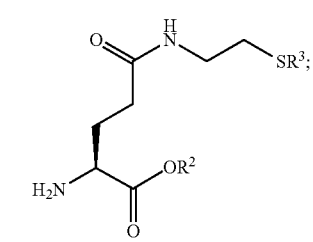

(IXa)

and/or the compound of formula (X) may be a compound of formula (Xa):

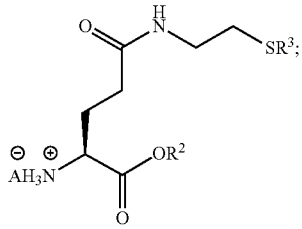

and/or
the compound of formula (VIII) may be a compound of formula (VIIIa):

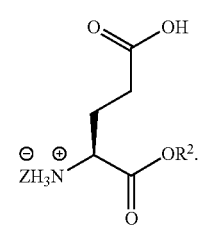

While A is indicated as a monovalent anion for convenience in formula (Xa), A may be a divalent or trivalent anion, in which case formula (Xa) is represented by formula (Xaα) or formula (Xaβ):

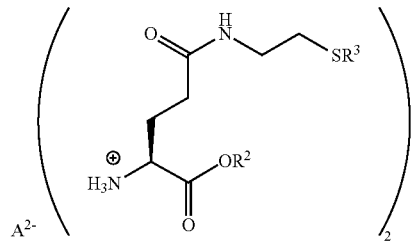

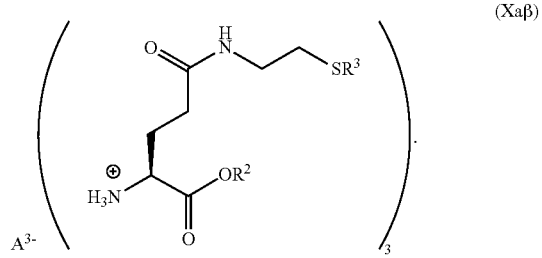

Unless indicated otherwise by the context, a reference to a compound of formula (Xa) includes reference to a compound of formula (Xaα) and/or (Xaβ).

EXAMPLES

The following examples demonstrate synthetic routes to prodrug derivatives of cysteamine.

Example 1—Synthetic Route to CF10

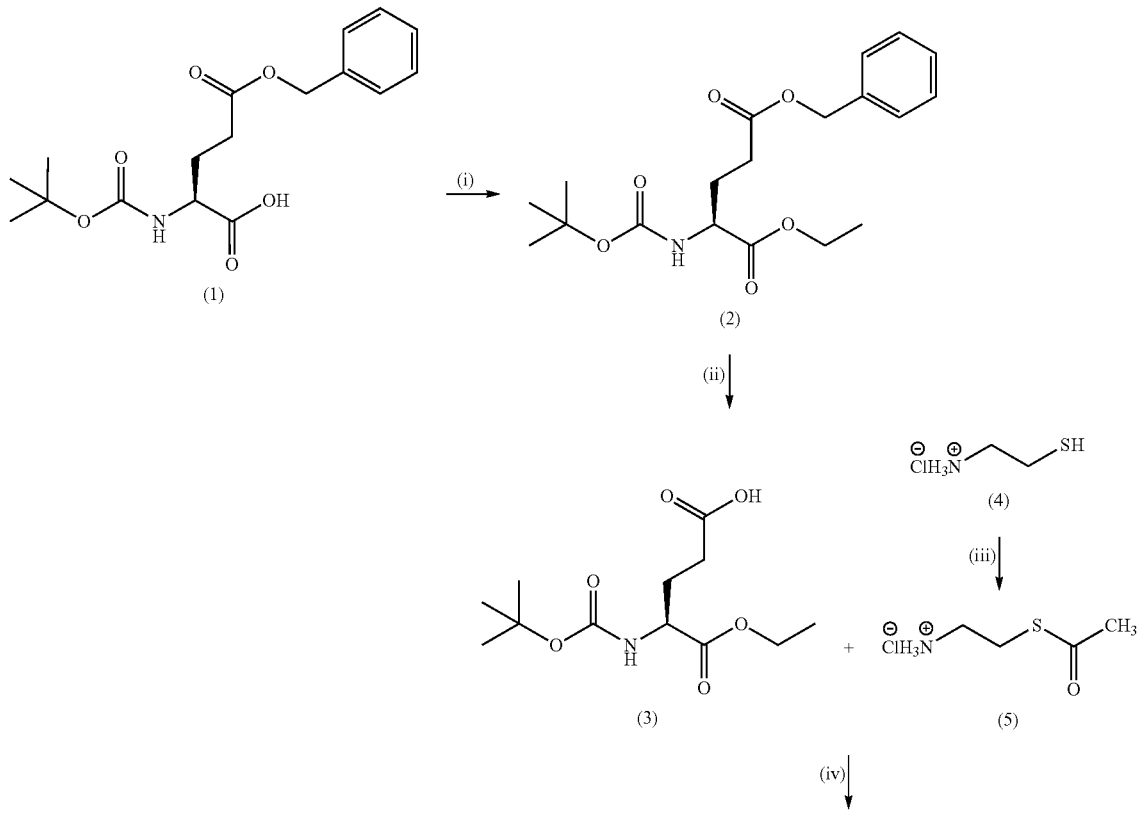

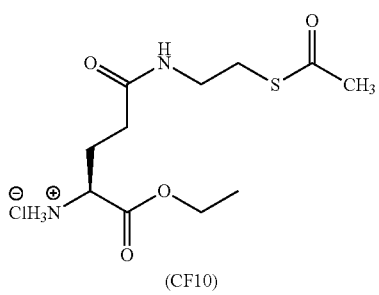

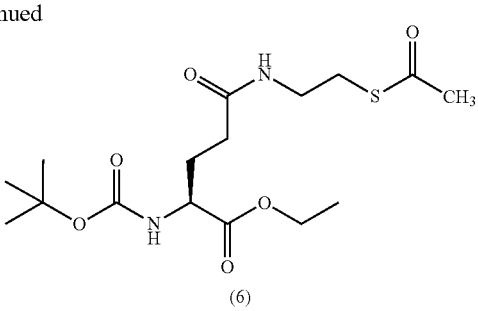

(CF10) (6)

(i) BrCH$_2$CH$_3$, K$_2$CO$_3$, DMF, RT, 4 h
(ii) Pd-C (10%), MeOH, H$_2$, RT, 4 Bar, 6 h
(iii) Acetyl Chloride, DCM, 40° C., 3 h
(iv) EDCI, HOBt, N-Methylmorpholine, DCM, 0° C.-RT, 18 h
(v) HCl (2M) in diethylether, RT, 4 h

Synthesis of 2-(S)-tert-Butoxycarbonylamino-pentanedioic Acid 5-benzyl Ester 1-ethyl Ester (2)

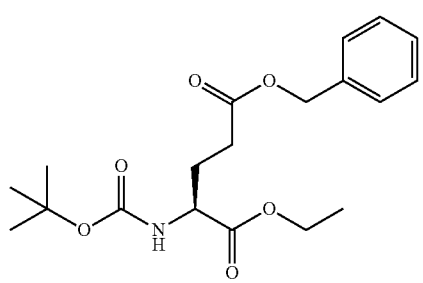

(2)

To a cooled solution of Boc-Glu(OBzl)-OH (1 mol equiv.) in DMF (1 g in 3.5 mL) at 5° C. was added K$_2$CO$_3$ (1.1 mol equivalents). The mixture was stirred for 10 mins before charging ethyl bromide (1.5 mol equiv.) and stirring for a further 30 mins at 5° C. The reaction mixture was warmed to room temperature and stirred out for a further 4 h. The mixture was then diluted with EtOAc, washed sequentially with water, brine, and concentrated under vacuum to give the crude product (2) (Yield ~97%) which was carried forward without further purification.

Synthesis of 2-(S)-tert-Butoxycarbonylamino-pentanedioic Acid 1-ethyl Ester (3)

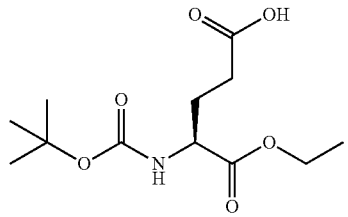

(3)

To a solution of Compound 2 (1 mol equivalent), was charged MeOH (1 g in 8 mL), followed by 10% Pd/C (50% H$_2$O, 0.012 mol equiv.). The mixture was then hydrogenated at 4 bar for 6 hours at 20 to 25° C. Upon completion of the reaction, the catalyst was removed by filtration before concentrating the solution under vacuum at 40° C. to give the crude product (3) (Yield ~100%) which was used in the next step without any further purification.

Synthesis of 1-[(2-Aminoethyl)sulfanyl]ethan-1-one Hydrochloride (5)

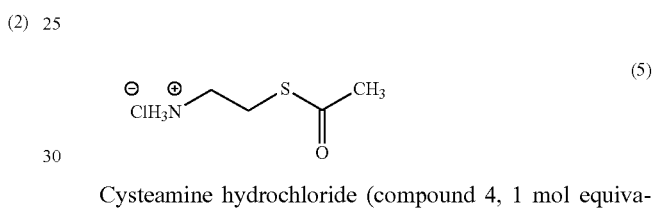

(5)

Cysteamine hydrochloride (compound 4, 1 mol equivalent) was suspended in CH$_2$Cl$_2$ (1 g in 5 mL). Acetyl chloride (2.0 mol equiv.) was then added over 15 mins. The mixture was then heated at reflux (40° C.) for 3 h before cooling back to room temperature. The resulting solid was collected by filtration then washed with CH$_2$Cl$_2$ and dried under vacuum to give a white crystalline solid. The crude material was recrystallised from isopropyl alcohol and H$_2$O, isolated by filtration, then washed with isopropyl alcohol at 5° C. After drying under vacuum at 50° C. a white crystalline solid (5) was obtained (Yield ~64%); m.p. 146 to 148° C.

Synthesis of 4-(2-Acetylsulfanyl-ethylcarbamoyl)-2-(S)-tert-butoxycarbonylamino-butyric Acid Ethyl Ester (6)

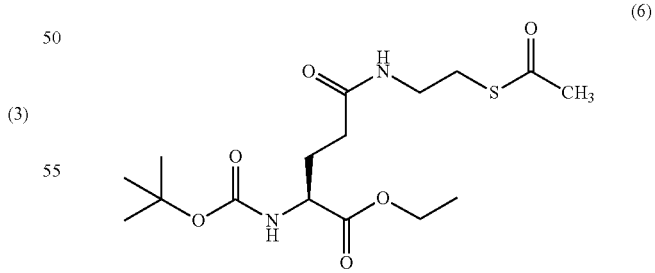

(6)

Compound 3 (1 mol equivalent) was dissolved in dry DCM (1 g in 20 mL) and to this was added HOBt (1.2 mol equiv.) and 1-ethyl-3-(3-dimethylaminopropyl)carbodiimide (EDCI) (1.2 mol equiv.). The mixture was stirred for 5 mins, charged with N-methyl morpholine (0.8 mol equiv.) and stirred for a further 15 mins at 0° C. Compound 5 (1 mol equiv.) was then added and the mixture stirred for an additional 45 mins at 0° C., before warming gradually to room temperature and left to stir for 18 h. The solution was then washed sequentially with aqueous sodium bicarbonate (5% w/v), aqueous citric acid (10% w/v) and brine, and concentrated under vacuum at 30° C. to give the crude product (6) as a white solid (Yield ~64%).

Synthesis of 4-{[2-(S)-(Acetylsulfanyl)ethyl]carbamoyl}-1-ethoxy-1-oxobutan-2-aminium Chloride [CF10]

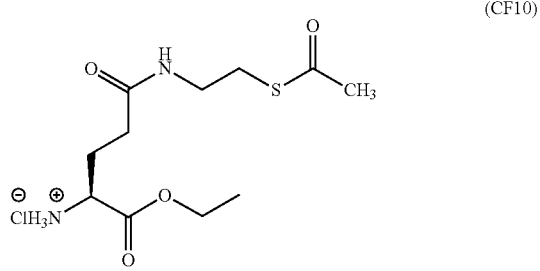

(CF10)

Compound 6 (1 mol equivalent) was stirred in HCl (2 M) in diethyl ether overnight (1 g in 8.66 mL). The slurry was stirred for 18 h, filtered and the solid washed with diethyl ether to give the crude product as a fine white powder. The crude product was slurried in isopropyl alcohol at 40° C. before cooling back to 0 to 5° C. The product was then collected by filtration, washed with isopropyl alcohol, diethyl ether, and dried under vacuum at 35° C. to give CF10 as a fine white powder (Yield ~76%).

Example 2—Alternative Synthetic Route to CF10 and Related Salts

The method comprises forming the free base of CF10 prior to conversion into the salt form, as set out in the following reaction scheme:

In this reaction scheme the cysteamine ($NH_2CH_2CH_2SH$) starting material may be provided as a base, as indicated above, or in a pharmaceutically acceptable salt form, such as cysteamine hydrochloride. The method of example 2 may provide a number of benefits. For example, because the free base is formed before the salt form, any acid that provides an appropriate anion, e.g. pharmaceutically acceptable anion, may be used for the final step. This provides a method to obtain salt forms of CF10 with various desired anions. In addition, while the salt form is typically desired, as the salt form will usually have a longer shelf life than the free amine base, if the free amine base is desired it is also possible to isolate the CF10 free base. The method of example 2 may also provide other improvements over the methods disclosed in L. Frost et al., *Eur. J. Med. Chem.*, 2016, 109, 206-215, such as improvements in yield, purity, and/or tractability, etc.

Example 3—Further Synthesis of CF10 and Related Salts

Synthesis of 2-(S)-tert-Butoxycarbonylamino-pentanedioic Acid 5-benzyl Ester 1-ethyl Ester (2)

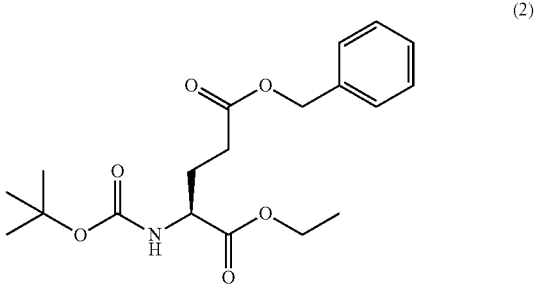 [SMILES: CCOC(=O)[C@H](CCC(=O)OCc1ccccc1)NC(=O)OC(C)(C)C]

(2)

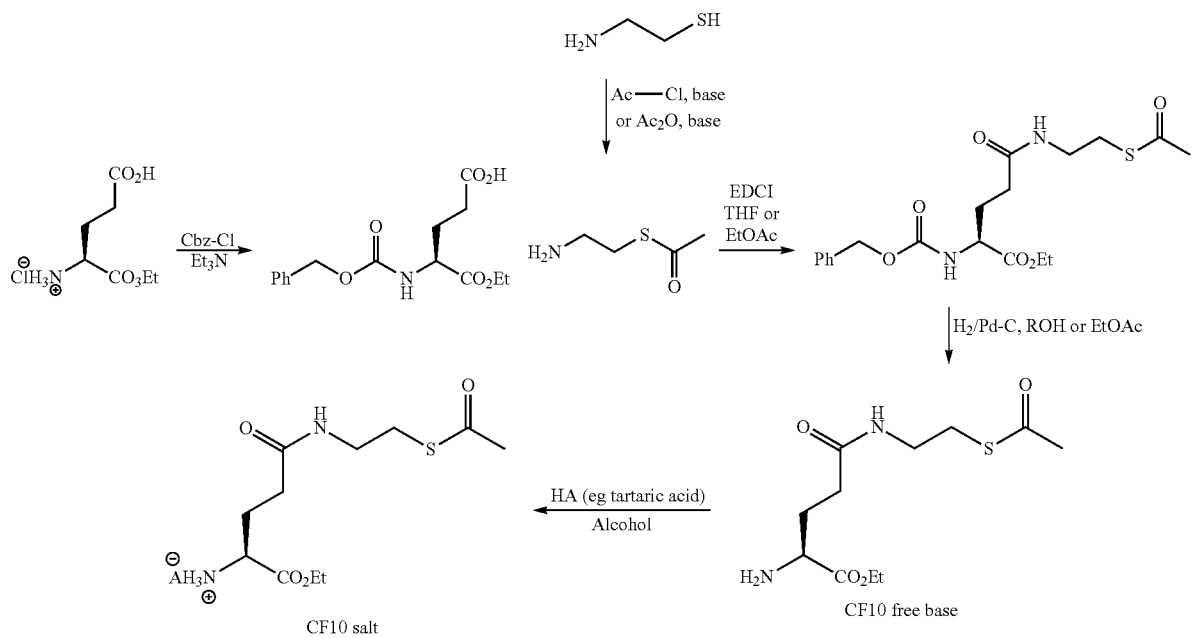

K₂CO₃ (1.1 eq.) was added to a cooled solution of Boc-Glu(OBzl)-OH (1 eq.) in DMF (1.14 L) at 5° C. The mixture was stirred for 10 min s before charging with ethyl bromide (1.5 eq.) and stirred for a further 30 mins at 5° C. The reaction mixture was warmed to room temperature and stirred for a further 4 hrs. The mixture was then diluted with EtOAc (1.14 L), washed with water (2×1.14 L), brine (1.14 L), and concentrated under vacuum to give (2) (Yield ~97%) which was used without further purification.

Synthesis of 2-(S)-tert-Butoxycarbonylamino-pentanedioic Acid 1-ethyl Ester (3)

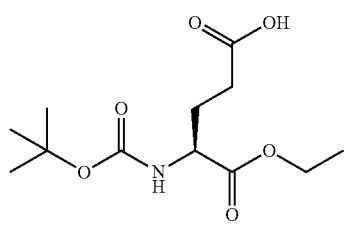

(3)

2-(S)-tert-Butoxycarbonylamino-pentanedioic acid 5-benzyl ester 1-ethyl ester (2) (90 g, 0.25 mol) and 10% Pd/C (50% H₂O, 6.0 g, 0.003 mol) were added to MeOH (700 mL). The mixture was hydrogenated at 4 bar for 6 h at 20 to 25° C. Upon completion of the reaction, the Pd/C catalyst was removed by filtration and the resulting solution concentrated under vacuum at 40° C. to give the crude product (3) (68 g, 0.25 mol, Yield ~100%) which was used in the next step without any further purification.

Synthesis of 1-[(2-Aminoethyl)sulfanyl]ethan-1-one Hydrochloride (5)

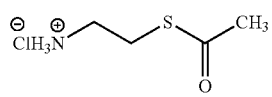

(5)

Cysteamine hydrochloride (compound 4, 1 mol equiv.) was suspended in CH₂Cl₂ (5 vol equiv.) and treated with acetyl chloride at reflux over 30 mins. The mixture was heated at reflux for a further 4 h before cooling to room temperature. The resulting solid was then collected by filtration then washed with CH₂Cl₂ (2.5 vol eq.). The wet cake was treated with CH₂Cl₂ (5 vol equiv.) for 30 mins at reflux, then cooled to room temperature. The resulting solid was collected by filtration and then washed with CH₂Cl₂ (2.5 vol equiv.). The subsequent wet cake was further treated with CH₂Cl₂ (5 vol equiv.) for 30 mins at reflux, then cooled to room temperature. The resulting solid was collected by filtration and then washed with CH₂Cl₂ (2.5 vol equiv.). After drying under vacuum, a white solid (5) was obtained (Yield ~96.4%).

Synthesis of 4-(2-Acetylsulfanyl-ethylcarbamoyl)-2-(S)-tert-butoxycarbonylamino-butyric Acid Ethyl Ester (6)

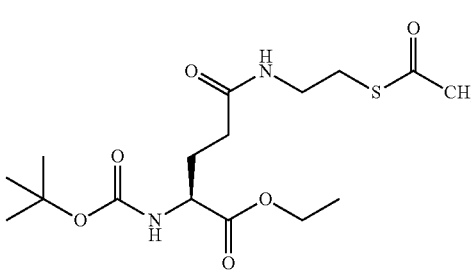

(6)

2-(S)-tert-Butoxycarbonylamino-pentanedioic acid 1-ethyl ester (3) (1 mol equiv.) in dry dichloromethane (175 mL) was chilled to 0° C. under nitrogen. A solution of Dicyclohexylcarbodiimide (1.25 mol equiv.) dissolved in dichloromethane (125 mL) was charged to the 2-(S)-tert-butoxycarbonylamino-pentanedioic acid 1-ethyl ester solution, maintaining a temperature of 0° C. and stirred for 15 mins. 1-[(2-Aminoethyl)sulfanyl]ethan-1-one hydrochloride (5) (1 mol equiv.) and N-methylmorpholine (1 mol equiv.) were then added to the reaction mixture and this was maintained at a temperature of 0° C. The reaction mixture was stirred overnight allowing to reach room temperature. The slurry was filtered, washed with dichloromethane and the combined filtrates washed sequentially with aqueous citric acid (10% w/v), aqueous sodium bicarbonate solution (5% w/v), then brine before concentrating. The material was triturated with isopropyl acetate (100 mL) and filtered. The filtrate was charged with n-heptane, cooled to −5° C. to 5° C. and a crystallisation seed was added. The batch was stirred at 0° C. for 1-2 h and then filtered. The resultant solids were washed with a mixture of isopropyl acetate:n-heptane (1:2 v/v) and dried under vacuum at 35-40° C. to yield the desired product (6) (Yield ~62%).

Synthesis of Ethyl 4-{[2-(acetylsulfanyl)ethyl]carbamoyl}-(2S)-aminobutanoate Hydrochloride (CF10)

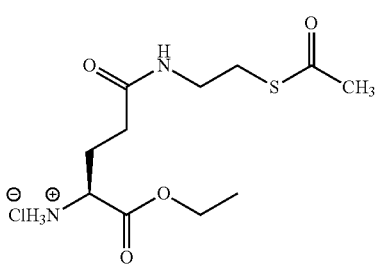

(CF10)

4-(2-Acetylsulfanyl-ethylcarbamoyl)-2-(S)-tert-butoxycarbonylamino-butyric acid ethyl ester (6) (25 g, 0.06 mol) was stirred in acetyl chloride/isopropyl alcohol/isopropyl acetate mixture at ambient temperature overnight until a slurry was formed. The slurry was filtered, washed with isopropyl acetate (30 mL) and then reslurried in warm isopropyl acetate, cooled and filtered. The filter cake was washed with isopropyl acetate and the resulting solid dried under vacuum, yielding a white solid CF10 (Yield ~79%).

The method of example 3 may provide a number of benefits. For example, this synthesis provides a readily scalable route to CF10 and has a good impurity profile. Additionally, the reactants and intermediates used in this synthesis provide improved handling characteristics.

The invention claimed is:

1. A method of forming a compound of formula (X), the method comprising reacting the compound of formula (III) with the compound of formula (V) to form the compound of formula (VI):

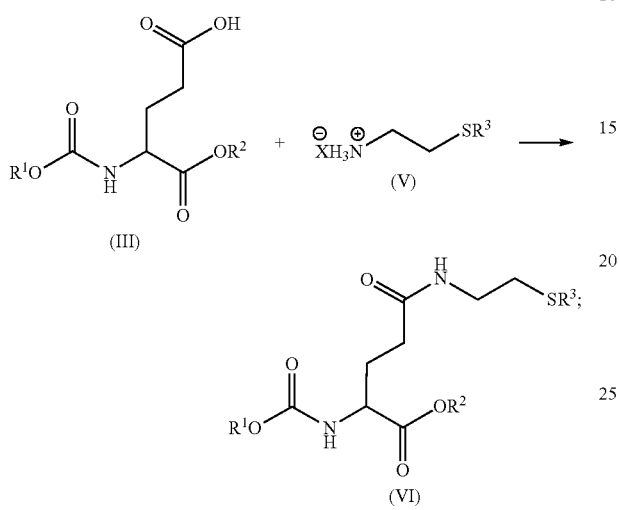

and
cleaving the $R^1$-oxycarbonyl amide of the compound of formula (VI) with a strong acid of the formula HA to form the compound of formula (X):

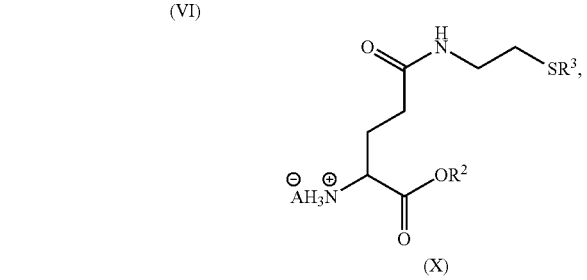

wherein
$R^1$ is —C(CH$_3$)$_3$;
$R^2$ is selected from —H, —C$_1$-C$_4$-alkyl, —C$_2$-C$_4$-alkenyl and C$_1$-C$_4$-alkyl-aryl;
$R^3$ is selected from —C(O)H and —C(O)C$_1$-C$_4$-alkyl;
X is a halide; and
A is a halide or other counterion of the strong acid, wherein reacting the compound of formula (III) with the compound of formula (V) is performed in the presence of a base having a pK$_a$ in water of less than 9.

2. The method of claim 1, wherein the compound of formula (III) is a compound of formula (IIIa):

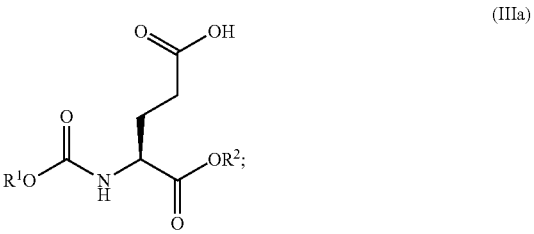

the compound of formula (VI) is a compound of formula (VIa):

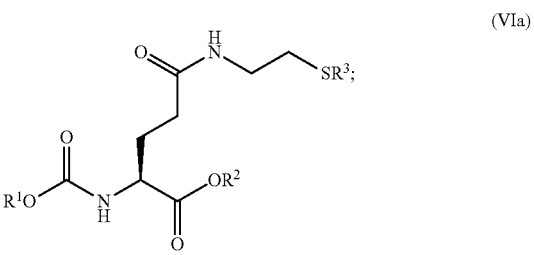

and
the compound of formula (X) is a compound of formula (Xa):

3. The method of claim 1, wherein $R^2$ is —C$_1$-C$_4$-alkyl.

4. The method of claim 1, wherein $R^2$ is —C$_1$-C$_4$-alkyl-aryl.

5. The method of claim 1, wherein $R^3$ is —C(O)C$_1$-C$_4$-alkyl.

6. The method of claim 1, wherein the acid is formed in situ.

7. The method of claim 1, wherein A is selected from chloride or bromide.

8. The method of claim 1, wherein the compound of formula (V) is formed by adding a protecting group of formula —$R^3$ to the thiol group of formula (IV)

9. The method of claim 1, wherein the compound of formula (III) is formed by reducing a compound of formula (II):

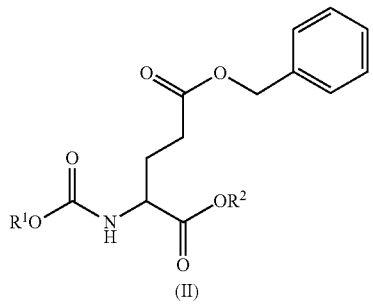
(II)

→

(III)

10. The method of claim 9, wherein the compound of formula (II) is a compound of formula (IIa):

(IIa)

and the compound of formula (III) is a compound of formula (IIIa):

(IIIa)

11. The method of claim 9, wherein the compound of formula (II) is formed by (i) reacting a compound of formula (I) with an alkylating reagent of formula halo-R²:

(I)

(i) →

(II)

12. The method of claim 11, wherein the compound of formula (I) is a compound of formula (Ia):

(Ia)

and the compound of formula (II) is a compound of formula (IIa):

(IIa)

13. The method of claim 1, wherein the base used in reacting the compound of formula (III) or formula (IIIa) with the compound of formula (V) is provided in an amount of not more than 0.9 mol equiv. compared to the amount of the compounds of formulae (III) and (V), or the amount of the compounds of formulae (IIIa) and (V).

14. The method of claim 3, wherein $R^2$ is —$CH_2CH_3$.
15. The method of claim 4, wherein $R^2$ is —$C_1$-$C_4$-alkyl-phenyl.
16. The method of claim 5, wherein $R^3$ is —$C(O)CH_3$.
17. The method of claim 6, wherein the acid is formed in situ by reaction of an acyl halide with an alcohol.
18. The method of claim 7, wherein A is chloride.

* * * * *